US009039175B2

(12) United States Patent
Yatagai et al.

(10) Patent No.: US 9,039,175 B2
(45) Date of Patent: May 26, 2015

(54) THREE-DIMENSIONAL RETINA IMAGE GENERATION DEVICE

(75) Inventors: Toyohiko Yatagai, Utsunomiya (JP); Cense J. Abraham, Utsunomiya (JP)

(73) Assignee: UTSUNOMIYA UNIVERSITY, Utsunomiya-shi, Tochigi (JP)

( * ) Notice: Subject to any disclaimer, the term of this patent is extended or adjusted under 35 U.S.C. 154(b) by 180 days.

(21) Appl. No.: 13/388,075

(22) PCT Filed: Aug. 3, 2010

(86) PCT No.: PCT/JP2010/063057
§ 371 (c)(1),
(2), (4) Date: Feb. 28, 2012

(87) PCT Pub. No.: WO2011/016437
PCT Pub. Date: Feb. 10, 2011

(65) Prior Publication Data
US 2012/0147326 A1    Jun. 14, 2012

(30) Foreign Application Priority Data
Aug. 4, 2009    (JP) .................................. 2009-181893

(51) Int. Cl.
*A61B 3/14* (2006.01)
*A61B 3/10* (2006.01)
*A61B 3/12* (2006.01)

(52) U.S. Cl.
CPC ............... *A61B 3/1225* (2013.01); *A61B 3/102* (2013.01)

(58) Field of Classification Search
USPC .................. 351/200, 204–206, 209–210, 246
See application file for complete search history.

(56) References Cited

U.S. PATENT DOCUMENTS 5,777,719 A    7/1998  Williams et al.
7,488,070 B2 *  2/2009  Hauger et al. ................ 351/200
(Continued)

FOREIGN PATENT DOCUMENTS

JP    2001-507258    6/2001
JP    2005-501587    1/2005
(Continued)

OTHER PUBLICATIONS

Yoshiaki Yasuno, "Fourier Domain Coherence Optical Tomography System and Property," Applied Physics, vol. 75, No. 6, pp. 707-712 (2006), and English Summary.
V. Shidlovski, "Superluminescent Diodes. Short overview of device operation principles and performance parameters." SuperlumDiodes Ltd., 2004.
J. Jonkman et al., "Resolution in Optical Microscopy," Biophotonics, Methods in Enzymology, vol. 360, 2003, pp. 416-446.
(Continued)

*Primary Examiner* — Scott J Sugarman
*Assistant Examiner* — Robert E Tallman
(74) *Attorney, Agent, or Firm* — Drinker Biddle & Reath LLP

(57) ABSTRACT

An optical coherence eye-fundus tomography device has a high resolution and a good operability, as well as be miniaturized and be produced at a low cost. The optical coherence eye-fundus tomography device includes: a light source unit which emits a source light beam; a reference-light unit which reflects a reference light beam; an inspection unit which illuminates an object with an object scanning light beam, reflected the object scanning light beam; and a detection unit which obtains a tomographic image of the object on the basis of the interference light beam produced by interfering the reflected reference light beam with the reflected object light beam. For example, the light source unit emits the outgoing light beam that has a depth of focus of not less than 300 μm, and resolution that is 6 μm×6 μm or higher in a planar direction perpendicular to a traveling direction of the outgoing light beam.

8 Claims, 6 Drawing Sheets

(56) References Cited

U.S. PATENT DOCUMENTS

| | | | |
|---|---|---|---|
| 2007/0258095 A1* | 11/2007 | Olivier et al. | 356/479 |
| 2008/0002211 A1 | 1/2008 | Park et al. | |
| 2008/0049232 A1 | 2/2008 | Vakoc et al. | |
| 2008/0231807 A1 | 9/2008 | Lacombe et al. | |
| 2008/0309873 A1 | 12/2008 | Levecq et al. | |
| 2009/0149742 A1 | 6/2009 | Kato et al. | |

FOREIGN PATENT DOCUMENTS

| | | |
|---|---|---|
| JP | 2006-250826 | 9/2006 |
| JP | 2007-14569 | 1/2007 |
| JP | 2007-521866 | 8/2007 |
| JP | 2009-504294 | 2/2009 |
| JP | 2009-524066 | 6/2009 |
| JP | 2009-142313 | 7/2009 |
| JP | 2010-501877 | 1/2010 |

OTHER PUBLICATIONS

D. Piston, "*Concepts in Imaging and Microscopy*—Choosing Objective Lenses: The Importance of Numerical Aperture and Magnification in Digital Optical Microscopy," Biol. Bull., vol. 195, Aug. 1998, pp. 1-4.

E. Keller et al., "Light Microscopy (Excerpt from Chapter 1)," Cold Spring Harbor Laboratory Press, 2006, pp. 1-16.

Nikon MicroscopyU—Concepts and Formulas—Resolution, http://www.microscopyu.com/print/articles/formulas/formulasresolution-print.html, pp. 1-3 printed from the Internet on Mar. 3, 2014.

Nikon MicroscopyU—Concepts and Formulas—Depth of Field/Focus, http://www.microscopyu.com/print/articles/formulas/formulasfielddepth-print.html, pp. 1-3 printed from the Internet on Mar. 3, 2014.

* cited by examiner

THREE-DIMENSIONAL RETINA IMAGE GENERATION DEVICE

FIELD OF THE INVENTION

The present invention relates to an image generator for optical measurement of retina.

BACKGROUND ART

In recent year, researches on an optical coherence tomograph (OCT) which visualizes the depth structure of the inside of a living body using an interference effect of light are being advanced.

In particular, recently, an optical coherence eye-fundus tomography device capable of observing a three-dimensional image of the inside of a retina has been appeared, which works well when diagnosing diseases which may lead to blindness.

Conventionally, a low-coherence interferometer is used as one of such optical coherence eye-fundus tomography devices. As such optical coherence eye-fundus tomography devices, a time domain optical coherence eye-fundus tomography device (Time-Domain OCT (hereinafter, referred to as "TD-OCT")) is known which visualizes the depth structure of the inside of a living body based on an interfering signal of an object in the depth direction obtained by mechanically manipulating the reference optical path length.

The TD-OCT has a low coherence light source having a wide wavelength width, and split a light beam from the light source into two beams, and irradiates one of the two beams on an object, "an eyeball."

The TD-OCT scans the object in the depth direction using the one of the two beams (hereinafter, referred to as "object scanning light beam" or "probe light beam"). Further, the TD-OCT performs interference of the object scanning light beam and the other split beam of the two beams, which is a beam for reference (hereinafter, referred to as "reference light beam"). The TD-OCT detects the scattering position of the object based on the interference fringe pattern generated by interference of the object scanning light beam and the reference light beam.

The TD-OCT scans an object by sweeping the object scanning light beam in a cross direction with respect to the optical path of the object scanning light beam, or by moving the object in a cross direction with respect to the optical path, and then, obtains an image of the cross-section of the object (See, for example, Non-Patent Document 1).

On the other hand, a spectrum domain OCT (Fourier Domain OCT (hereinafter, referred to as "FD-OCT")) which performs interference of light waves on a Fourier space (spectrum domain) not on a real space (time domain), without using such mechanical scanning in the depth direction, is known. The FD-OCT has a measurement speed several tens of times, compared with the TD-OCT.

Similar to the TD-OCT, the FD-OCT calculates the resolution of an object in the depth direction, using two split light beams and a low-coherence interference principle. However, in the FD-OCT a reference light beam and an object scanning light beam which scans an object enter a spectroscope in a parallel, and dispersed simultaneously in the spectroscope to perform interference in a spectrum domain.

The FD-OCT measures a spectral interference fringe generated by the interference by a CCD, and performs a Fourier transform on the spectral interference fringe. As a result, the FD-OCT obtains the reflection distribution of an object in the depth direction.

In particular, the FD-OCT irradiates measure points on a retina forming surface with the object scanning light beam by driving a galvano-mirror in order to obtains a three-dimensional tomographic image. Since the FD-OCT can obtain a three-dimensional tomographic image only by two-dimensional mechanical scanning, a high speed tomographic measurement can be performed (see, for example, Non-Patent Document 1).

In addition to the above-mentioned OCTs, a wavelength sweeping OCT (i.e., swept source OCD (hereinafter, referred to as "SS-OCT") is also known which makes a spectroscope needless by sweeping the oscillation wavelength of a light source and sweeping the wavelength of the light source (see, for example, Non-Patent Document 1).

PRIOR ART REFERENCES

Non-Patent Document

Non-Patent Document 1: YASUNO Yoshiaki, "Fourier Domain Optical Coherence Tomography", *Applied Physics*, Vol. 75, Number 6, pp. 707-712 (2006).

SUMMARY OF THE INVENTION

The Problems Solved by the Invention

However, the above-mentioned variety of OCTs do not have an enough image resolving power, which makes it difficult to perform an initial diagnosis of diseases such as age-related macular degeneration and glaucoma, and a further shortening of the inspection time is demanded.

The present invention is devised to resolve the above problems, and an object thereof is to provide a three-dimensional retina image generator which has a high resolution and a good operability, as well as be miniaturized and be produced at a low cost.

Problem Resolution Unit (1) A three-dimensional retina image generator of the present invention for solving the above-described problems, splits an outgoing light beam emitted from a light source to be individually irradiated on an object which is a retina of an eyeball to be measured and on a reference mirror, and generates a three-dimensional image of the object from data of an interference fringe obtained by superimposing an object light beam and a reference light beam, and the object light beam is reflected on the object and the reference light beam is reflected on the reference mirror. The three-dimensional retina image generator comprises: a light source unit having the light source; a light splitter that splits the outgoing light beam emitted from the light source into the reference light beam and the object light beam; a reference light beam unit that has the reference mirror and reflects the reference light beam; an adaptive optics measurement unit that irradiates the retina with the object light beam, and that outputs a light scattered on the retina as a reflected object light beam while compensating aberration generated due to the structure of the eyeball; a detecting unit that performs interference of the reflected reference light beam and the reflected object light beam, and that detects interference intensity in each of wavelengths of interfering light beam generated by performing the interference; a calculating unit that calculates reflected intensity data of the retina in a depth direction nearly parallel to an incident direction in which the object light beam enters the retina by performing a Fourier transform on the detected interference intensity in each of the wavelengths of interfering light beam; and a generation unit that generates the three-dimensional image of the retina based on the calculated reflected intensity data, wherein the adaptive optics measurement unit has: a wavefront sensor that detects a wavefront of the reflected object light beam; an image location adjusting unit that adjusts an image location of the object light beam based on the wavefront of the reflected object light beam detected by the wavefront sensor; and a beam angle adjusting unit that adjusts an angle of the object light beam with respect to the image location on the retina in order to scan the retina by the object light beam, and, and wherein the light source unit emits the outgoing light beam that has a depth of focus of not less than 300 μm, and resolution that is 6 μm×6 μm or higher in a planar direction perpendicular to a traveling direction of the outgoing light beam.

For example, when the depth required for a diagnosis of a retina is 300 μm or deeper, and when a light beam which has a resolution (azimuth resolution) in a planar direction perpendicular to a travelling direction of an object light beam of 6 μm×6 μm or higher is emitted, a reflected light beam is obtained which does not contain a complex aberration in a cornea, a crystalline lens o the like, and which only contains a simple aberration such as astigmatism. In other words, because the reflected light beam in which a wavefront aberration can be represented by third or lower order terms in Zernike polynomials is obtained, the wavefront aberrations can be easily corrected.

By employing the above-mentioned configuration, the three-dimensional retina image generator according to the present invention can use the object light beam which does not have a high order aberration in Zernike polynomials and which only has a low order aberration. Therefore, the three-dimensional retina image generator does not need components for correcting a higher aberration, and then, can be built using fewer components, as well as have a high resolution for the image of the retina by the emitted object light beam and a good operability.

Accordingly, the three-dimensional retina image generator according to the present invention can perform an accurate calculation of the interference intensity in each of wavelengths of the interfering light beam. Therefore, the three-dimensional retina image generator can generate an accurate three-dimensional image of the retina based on the calculated interference intensity data, as well as can improve loss of light quantity, be miniaturized and be produced at a low cost.

(2) The three-dimensional retina image generator of the present invention has the beam angle adjusting unit which comprises: a single scanning mirror that is capable of moving in two directions in order to sweep the object light beam in a first direction and in a second direction, the first direction being nearly parallel to a retina forming surface on which the retina is formed, the second direction being nearly parallel to the retina forming surface and nearly perpendicular to the first direction; and a galvanometer that controls movement of the scanning mirror in the first direction and the second direction.

By employing such a configuration, the three-dimensional retina image generator according to the present invention can sweep the object light beam on the retina using a single mirror. Therefore, the three-dimensional retina image generator can be built using fewer components, as well as can improve loss of light quantity, be miniaturized and be produced at a low cost.

(3) The three-dimensional retina image generator according to the present invention has the image location adjusting unit which comprises: a deformable mirror in which a mirror surface is deformed based on the wavefront of the reflected object light beam detected by the wavefront sensor, and a concave mirror that forms an image on the retina by focusing the object light beam reflected by the deformable mirror on the retina.

By employing such a configuration, the three-dimensional retina image generator according to the present invention can use the reflected object light beam in which the wavefront aberration can be represented by third or lower order terms in Zernike polynomials. Therefore, the three-dimensional retina image generator can use the reflected object light beam having the wavefront aberration which can be corrected by only a low order aberration and by only a deformable mirror without a high order aberration in Zernike polynomials.

Accordingly, the three-dimensional retina image generator according to the present invention can be built using fewer components, as well as can improve loss of light quantity, be miniaturized and be produced at a low cost.

(4) The three-dimensional retina image generator according to the present invention has the image location adjusting unit which comprises: a deformable mirror in which a mirror surface is deformed based on the wavefront of the reflected object light beam detected by a wavefront sensor, and a convex lens that forms an image on the retina by focusing the object light beam reflected by the deformable mirror on the retina.

By employing such a configuration, the three-dimensional retina image generator according to the present invention can use the reflected object light beam which has the wavefront aberration represented by third or lower order terms in Zernike polynomials. Therefore, the three-dimensional retina image generator can use the reflected object light beam having the wavefront aberration which can be corrected by only a low order aberration and by only the deformable mirror without a high order aberration in Zernike polynomials.

Accordingly, the three-dimensional retina image generator according to the present invention can be built using fewer components, as well as can improve loss of light quantity, be miniaturized and be produced at a low cost.

(5) The three-dimensional retina image generator according to the present invention is configured so that the wavefront of the reflected object light beam which is disturbed by moving the mirror surface of the deformable mirror.

By employing such a configuration, the three-dimensional retina image generator according to the present invention can reduce contrast of a speckle noise because the wavefront of the reflected object light beam can be disturbed by operating the deformable mirror.

(6) The three-dimensional retina image generator according to the present invention has the image location adjusting unit which comprises: a pair of convex lenses, distance between the convex lenses varies based on the wavefront of the reflected object light beam detected by the wavefront sensor, and a lens that forms an image on the retina by focusing the object light beam emitted from the pair of convex lenses.

By employing such a configuration, the three-dimensional retina image generator according to the present invention can use the reflected object light beam which has the wavefront aberration represented by third or lower order terms in Zernike polynomials. Therefore, the three-dimensional retina image generator can use the object reflected light having the wavefront aberration which can be corrected by only a low order aberration and by only varying the distance between the pair of convex lenses without a high order aberration in Zernike polynomials.

Accordingly, the three-dimensional retina image generator according to the present invention can be built using fewer components, as well as can improve loss of light quantity, be miniaturized and be produced at a low cost.

Efficacy of the Invention

By employing the above-mentioned configuration, three-dimensional retina image generator according to the present invention can use the object light beam which does not have a high order aberration in Zernike polynomials and which only has a low order aberration. Therefore, the three-dimensional retina image generator does not need components for correcting a higher aberration, and then, can be built using fewer components, as well as have a high resolution for the image of the retina by the emitted object light beam and a good operability.

Accordingly, the three-dimensional retina image generator according to the present invention can perform an accurate calculation of the interference intensity in each of wavelengths of the interfering light beam. Therefore, the three-dimensional retina image generator can generate an accurate three-dimensional image of a retina based on the calculated interference intensity data, as well as can improve loss of light quantity, be miniaturized and be produced at a low cost.

BRIEF DESCRIPTIONS OF THE DRAWINGS

FIG. 3(B) is a front view (B) of the two-axis galvanometer of the first embodiment.

Figure 4:
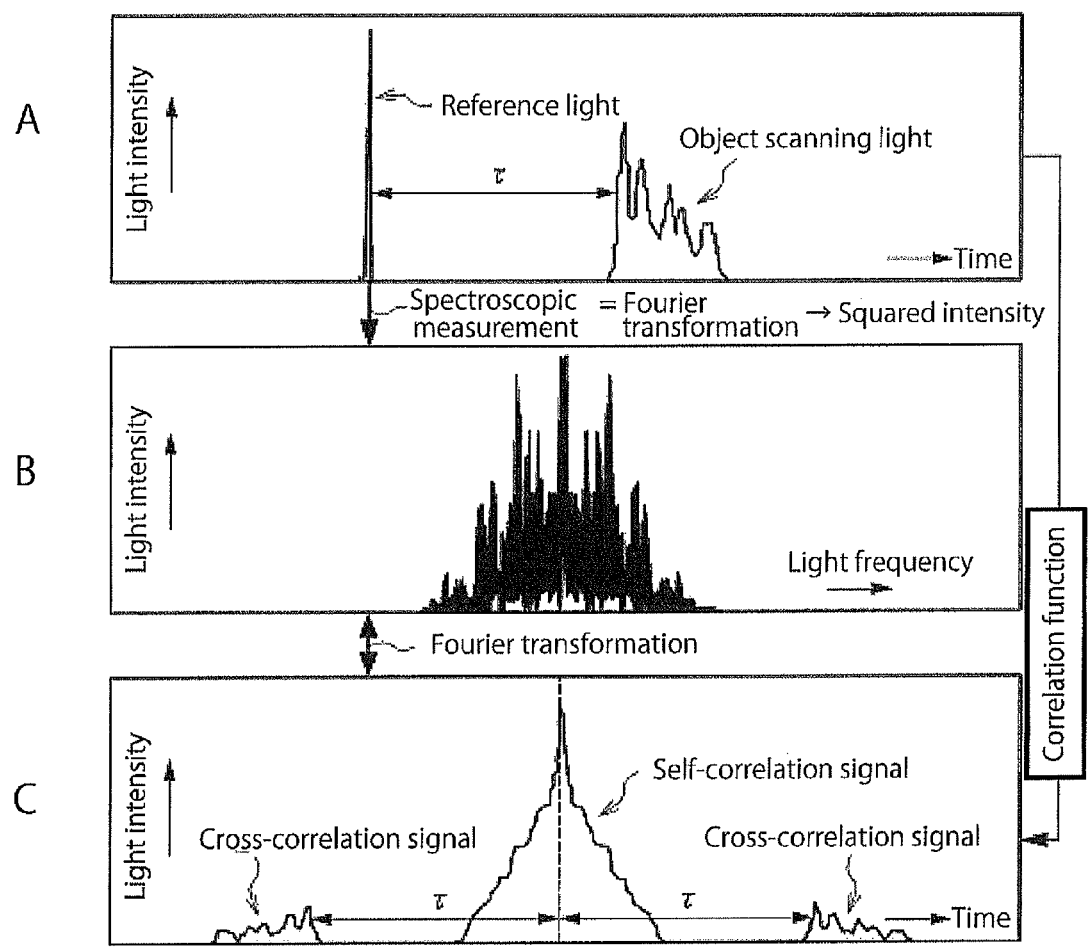

FIGS. 4 (A) to (C) are diagrams for explaining the calculation method of the interference intensities in a reflected reference light beam and a reflected object light beam.

Figure 5:
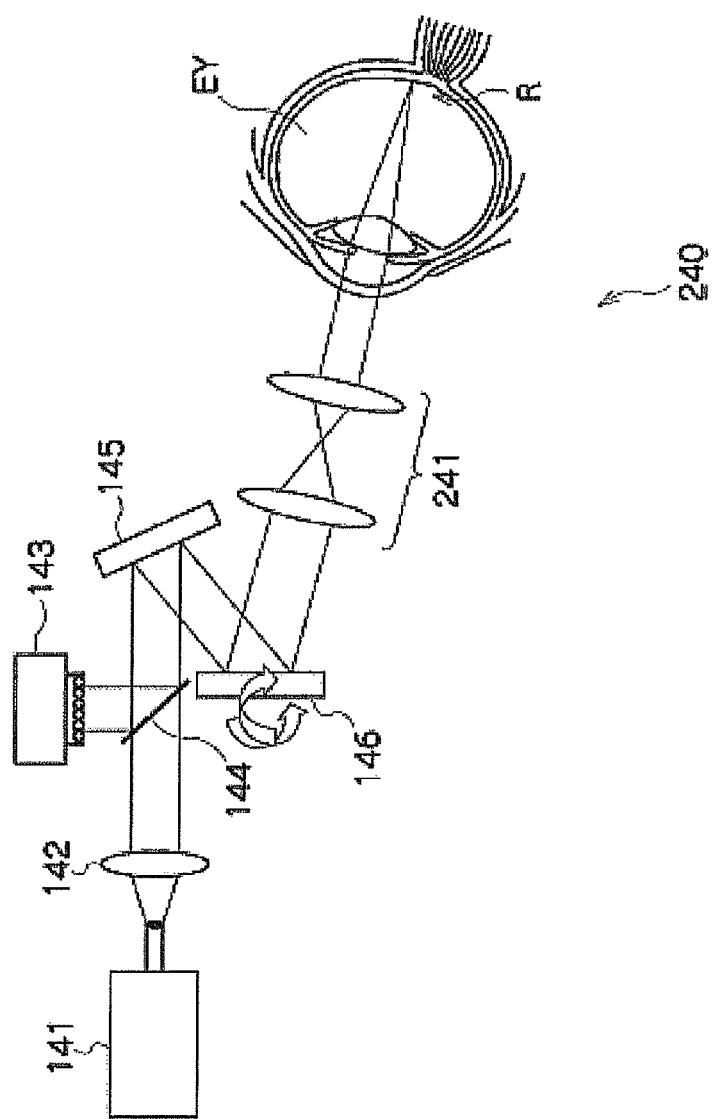

FIG. 5 is a block diagram illustrating the configuration in the second embodiment of an optical coherence eye-fundus tomography device according to the present invention.

Figure 6:
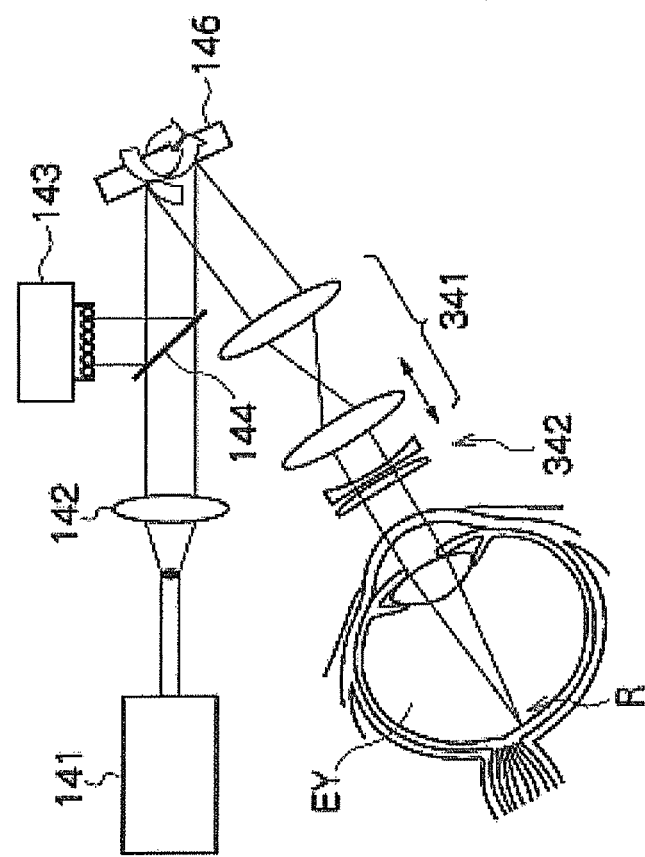

FIG. 6 is a block diagram illustrating the configuration in the third embodiment of an optical coherence eye-fundus tomography device according to the present invention.

EMBODIMENT OF THE INVENTION

In the following embodiments described below, a three-dimensional retina image generator of the present invention is applied to an optical coherence eye-fundus tomography device with adaptive optics (AO).

Specifically, the optical coherence eye-fundus tomography device (100), which splits an outgoing light beam emitted from a light source (111) to be individually irradiated on an object which is a retina (R) of an eyeball to be measured and on a reference mirror (RM), and generates a three-dimensional image of the object from data of an interference fringe obtained by superimposing an object light beam and a reference light beam, and the object light beam is reflected on the object and the reference light beam is reflected on the reference mirror (RM). The optical coherence eye-fundus tomography device (100) comprises: a light source unit (110) having the light source (111); a light splitter (120) that splits the outgoing light beam emitted from the light source (111) into the reference light beam and the object light beam; a reference light beam unit (130) that has the reference mirror (RM) and reflects the reference light beam; an adaptive optics measurement unit (140) which irradiates the retina (R) with the object light beam, and which outputs a light scattered on the retina (R) as a reflected object light beam while compensating the aberration generated due to the structure of the eyeball; a detecting unit (154) that performs interference of the reflected reference light beam and the reflected object light beam, and that detects interference intensity in each of the wavelengths of interfering light beam generated by performing the interference; a calculating unit (155) that calculates reflected intensity data of the retina (R) in a depth direction nearly parallel to an incident direction in which the object light beam enters the retina (R) by performing a Fourier transform on the detected interference intensity in each of the wavelengths of interfering light beam; and a generation unit (155) that generates the three-dimensional image of the retina (R) based on the calculated reflected intensity data, wherein the adaptive optics measurement unit (140) has: a wavefront sensor (143) that detects wavefront of the reflected object light beam; an image location adjusting unit (145, 147 (147a, 147b), 241, 341, 342) that adjusts an image location of the object light beam based on the wavefront of the reflected object light beam detected by the wavefront sensor (143); and a beam angle adjusting unit (146 (146a, 146b, 146c)) that adjusts an angle of the object light beam with respect to the image location on the retina (R) in order to scan the retina by the object light beam, and wherein the light source unit (110) emits the outgoing light beam that has a depth of focus of not less than 300 μm, and resolution that is 6 μm×6 μm or higher in a planar direction perpendicular to a traveling direction of the outgoing light beam.

Further, the optical coherence eye-fundus tomography device (100) has the beam angle adjusting unit (146 (146a, 146b, 146c)) which comprises: a single scanning mirror (146a) that is capable of moving in two directions in order to sweep the object light beam in a first direction and in a second direction, the first direction being nearly parallel to a retina forming surface on which the retina is formed, the second direction being nearly parallel to the retina forming surface and nearly perpendicular to the first direction; a galvanometer (146b, 146c) that controls movement of the scanning mirror in the first direction and the second direction.

Further, the optical coherence eye-fundus tomography device (100) has the image location adjusting unit (145, 147 (147a, 147b)) which comprises: a deformable mirror (145) in which a mirror surface is deformed based on the wavefront of the reflected object light beam detected by a wavefront sensor (143), and a concave mirror (147, (147a, 147b)) that forms an image on the retina by focusing the object light beam reflected by the deformable mirror on the retina (R).

Further, the optical coherence eye-fundus tomography device (100) has the image location adjusting unit (145, 241) which comprises: a deformable mirror (145) in which a mirror surface is deformed based on the wavefront of the reflected object light beam detected by a wavefront sensor (143), and a convex lens (241) that focus the object light beam reflected by the deformable mirror on the retina (R).

Further, the optical coherence eye-fundus tomography device (100) is configured so that the wavefront of the reflected object light beam is disturbed by moving the mirror surface of the deformable mirror (145).

Further, the optical coherence eye-fundus tomography device (100) has the image location adjusting unit (341, 342) which comprises: a pair of convex lenses (341), distance between the convex lenses varying based on the wavefront of the reflected object light beam detected by the wavefront sensor (143), and a lens (342) that forms an image on the retina by focusing the object light beam emitted from the pair of convex lenses on the retina (R).

Embodiments of the present invention will be described in detail with reference to the Figures.

First Embodiment

First, the first embodiment of an optical coherence eye-fundus tomography device according to the present invention will be described using FIGS. 1 to 4 (C).

To begin with, the configuration of optical coherence eye-fundus tomography device 100 of the present embodiment will be described using FIGS. 1 to 4 (C).

Figure 1:
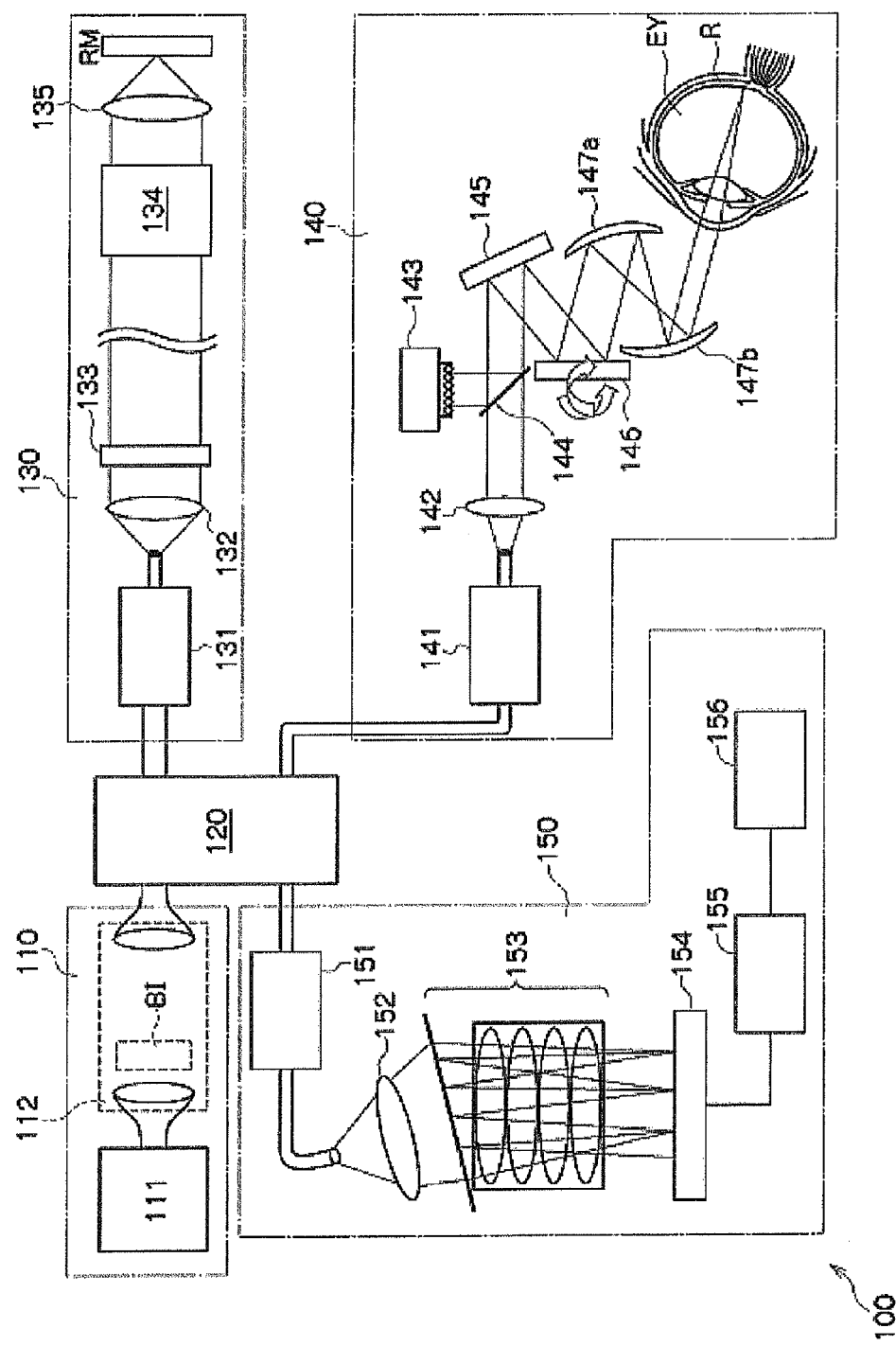
FIG. 1 is a block diagram illustrating the configuration of a first embodiment of an optical coherence eye-fundus tomography device according to the present invention.
Figure 2:
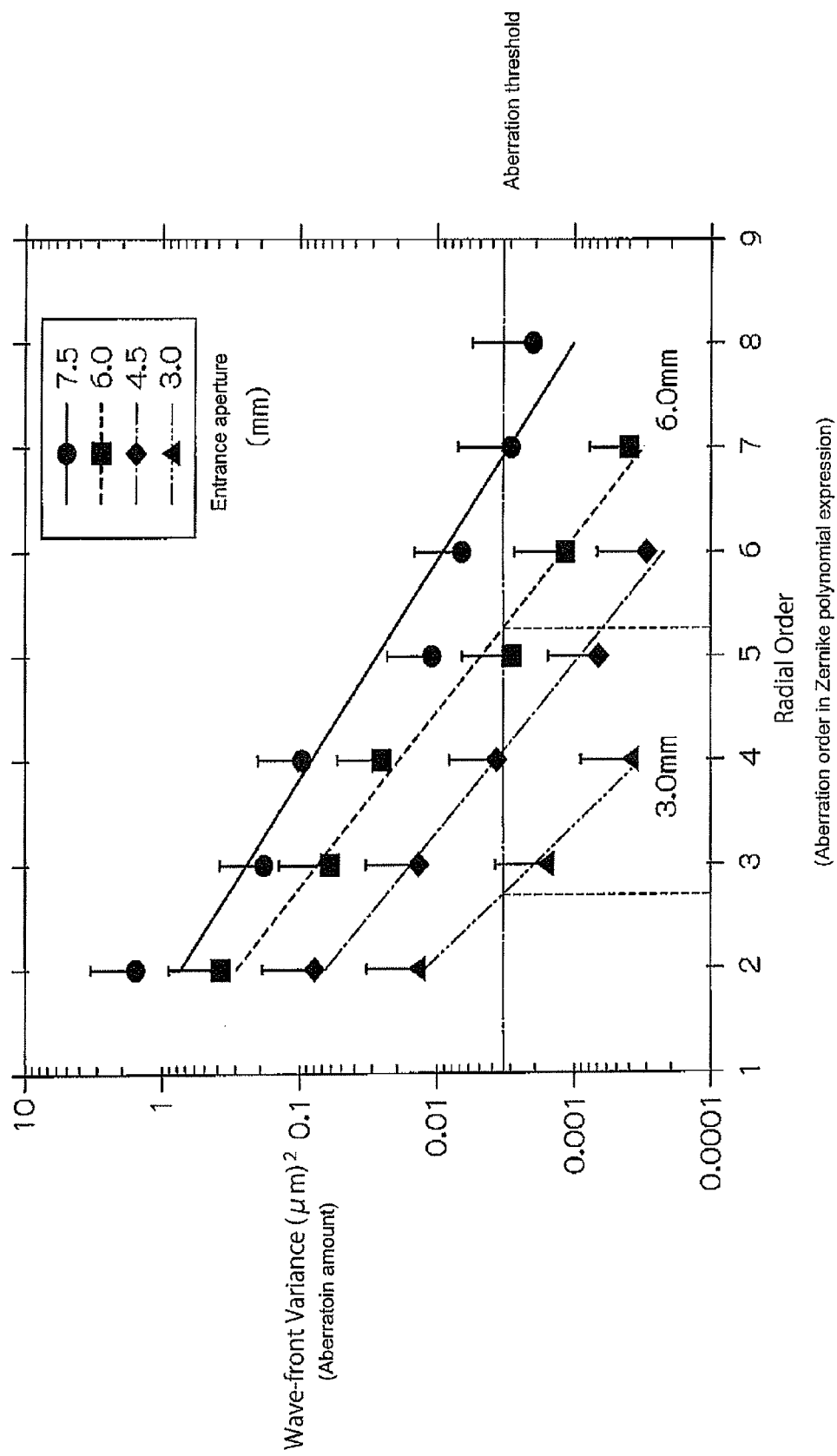
FIG. 2 is a graph of aberration amount of an eyeball of a healthy living body and aberration order in the Zernike polynomial expression.
Figure 3:
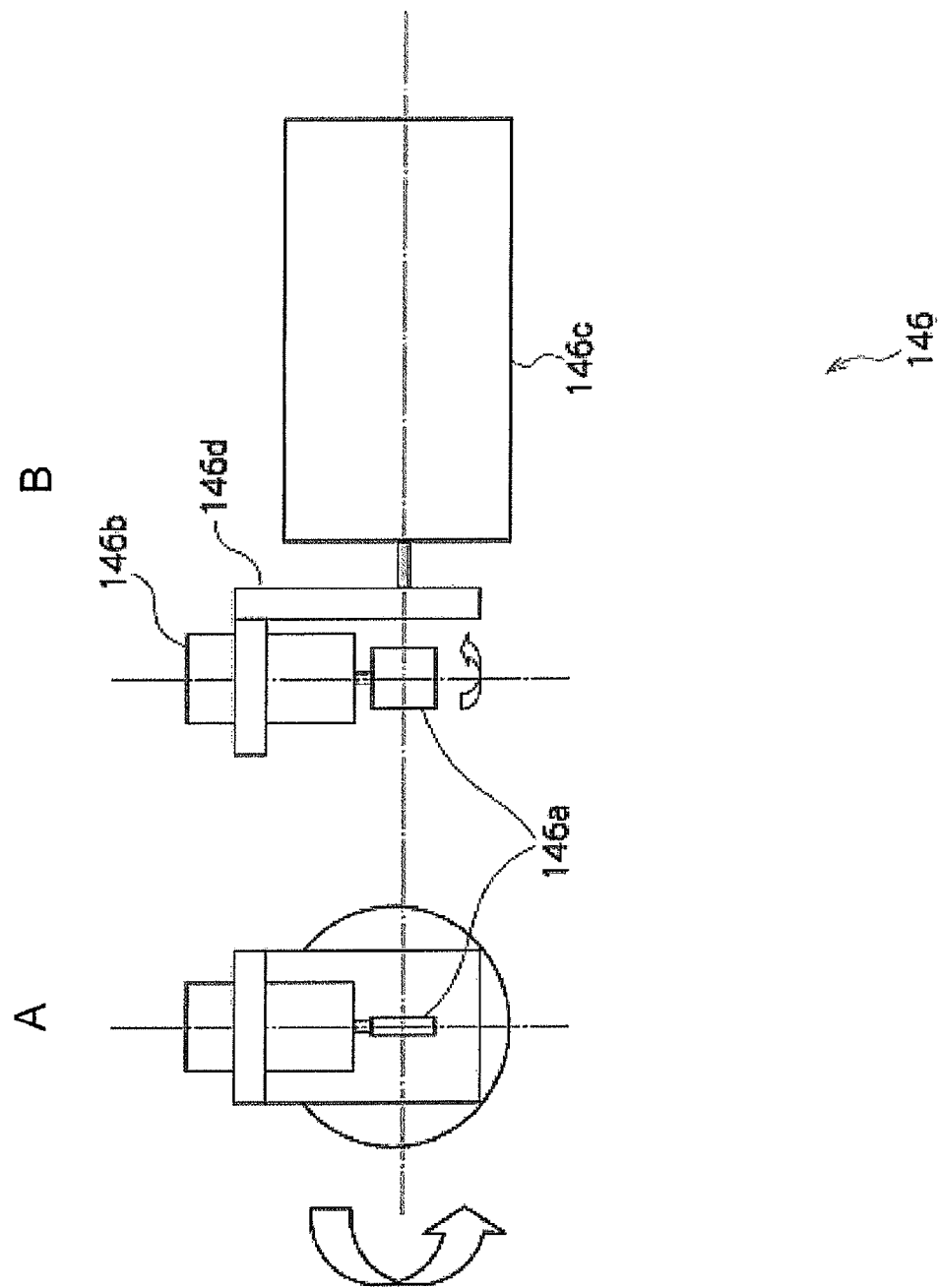
FIG. 3 (A) is a side view of a two-axis galvanometer of the first embodiment.

FIG. 1 is a block diagram illustrating the configuration of the present embodiment of optical coherence eye-fundus tomography device 100 according to the present invention. FIG. 2 is a graph of the aberration amount of an eyeball of a healthy living body and the aberration order in the Zernike polynomial expression. FIG. 3 (A) is a side view (A) of two-axis galvanometer 146 of the first embodiment, and FIG. 3(B) is a front view of two-axis galvanometer 146 of the first embodiment.

Optical coherence eye-fundus tomography device 100 of the present embodiment is an OCT-measuring device in which adaptive optics system (AO) technique is used, as well as a tomographic image of an object to be inspected (in the present embodiment, eyeball EY, in concrete, retina R) is obtained using the interference effect of light.

Optical coherence eye-fundus tomography device 100 splits a light source beam (hereinafter, referred to as "outgoing light beam") into an object scanning light beam (hereinafter, referred to as "object light beam") with which an inspection object is irradiated, and a reference light beam which is used as a reference when performing an interference measurement. Optical coherence eye-fundus tomography device 100 performs interference of a reflected object light beam, which is reflected when an object is irradiated with the object scanning light beam, and a reflected reference light beam which is the reference light beam reflected on a prescribed reflecting mirror RM.

In order to scan the retina R, optical coherence eye-fundus tomography device 100 sweeps the object scanning light beam in a first direction (transverse direction) which is nearly parallel to a retina forming surface on which retina R is formed, and in a second direction (longitudinal direction) which is nearly parallel to the retina forming surface and nearly perpendicular to the first direction. Optical coherence eye-fundus tomography device 100 generates a tomographic image of retina R including an image of a depth direction of retina R which is parallel to the travelling direction (optical axis direction) of the object scanning light beam, based on light beam generated by performing interference of the reflected object light beam and the reflected reference light beam for each point (hereinafter, referred to as "scanning point").

Specifically, as shown in FIG. 1, optical coherence eye-fundus tomography device 100 of the present embodiment has: light source unit 110 which emits the light source beam; and optical splitter/coupler 120 which splits the emitted light source beam into the reference light beam and the object scanning light beam, and performs interference of the reflected reference light beam and the reflected object light beam. For example, light source unit 110 of the present embodiment serves as a light source unit of the present invention, and optical splitter/coupler 120 serves as a light splitter.

Further, optical coherence eye-fundus tomography device 100 has: reference light unit 130 which reflects the reference light beam, and inputs a reflected reference light beam which is the reflected reference light beam into optical splitter/coupler 120; inspection unit 140 which irradiates an object with the object scanning light beam, and inputs a reflected object light beam which is the reflected object scanning light beam into optical splitter/coupler 120; and image detection unit 150 which obtains a tomographic image of an object based on a light beam (hereinafter, referred to as "interfering light beam") which is generated by performing interference of the reflected object light beam and the reflected reference light beam. For example, reference light unit 130 of the present embodiment serves as a reference light beam unit of the present invention, and inspection unit 140 serves as an adaptive optics measurement unit of the present invention. For example, image detection unit 150 of the present embodiment serves as a detecting unit, a calculating unit and a generation unit of the present invention.

Light source unit 110 emits light which is incoherent in time and incoherent in space.

For example, light source unit 110 of the present embodiment includes: irradiation source 111 which emits the light source beam; and calibration section 112 which has optical isolator BI, and which performs prescribed calibration using a glass with respect to the light source beam emitted from irradiation source 111.

Irradiation source 111 has a super luminescent diode, and emits a light beam having a wide wavelength width (for example, a wavelength having a width of about 150 nm), as a light source beam. Specifically, irradiation source 111 emits the light source beam which has a depth of focus of 300 μm or deeper and having a resolution (azimuth resolution) in the planar direction perpendicular to the travelling direction of the object scanning light beam of 6 μm×6 μm or higher.

The wavelength width of the light source beam is irrelevant to the depth of focus, and the wider the width, the better the resolution of the three-dimensional image in the depth direction improves. However, in view of a variety of influences, the wavelength width as described above is used. The upper limit of the depth of focus is not particularly limited, and is 400 μm as a realistic range. This is because an appropriate diagnosis can be performed with a depth of focus of 400 μm. Although the range of azimuth resolution is not particularly limited, the realistic maximum resolution is restricted by the maximum diameter of pupil, and is 3 μm×3 μm.

For example, irradiation source 111 of the present embodiment emits the light source beam having an entrance aperture of 3.0 mm as a near-infrared light source which is soft, and not glaring. When irradiation source 111 emits such a light source beam having an entrance aperture of 3.0 mm, an azimuth resolution of 6 μm×6 μm or higher can be obtained on retina R, and a depth of focus of about 390 μm can be obtained.

The entrance aperture of the light source beam emitted from irradiation source 111 of the present embodiment is not limited to 3.0 mm and may be about 3 mm. The entrance aperture defining the beam diameter depends on the wavelength of a light source, resolution, depth of focus or the like. For example, the larger the beam diameter, the better the resolution becomes. In this case, the beam diameter is smaller than when the beam diameter is small. On the other hand, the smaller the beam diameter, the worse the resolution becomes. However, the depth of focus is deeper than when the beam diameter is large. Namely, the entrance aperture is set keeping a balance among these. In the present invention, an object to be measured is a retina of an eyeball, and in this case, the entrance aperture is preferably about 3 mm, and may be, for example, 2.5 mm to 3.5 mm.

Further, as shown in FIG. 2, the measurement result of the aberration of eyeball EY of a healthy human being (healthy body) is indicated. In the case where a judgment standard which is the aberration threshold in the image quality, FIG. 2 indicates that only third order or lower aberrations are to be corrected when a light source beam is emitted by a diameter of about 3 mm.

As described above, in the present embodiment, the retina can be irradiated with the reflected object light beam which has enough azimuth resolution and depth of focus due to the wavefront aberration of the reflected object light beam represented by third or lower order terms in Zernike polynomials. Therefore, as described below, sufficient data of the interference intensity can be obtained, even when aberration correction in inspection unit 140 is made simple.

Calibration section 112 has optical isolator BI that transmits the light source beam, which is emitted by light source unit 110, only to optical splitter/coupler 120 and that does not transmit a backward light beam to the light source unit 110. Further, calibration section 112 performs a prescribed calibration on the light source beam.

Optical splitter/coupler 120 has a beam splitting prism, an optical fiber or the like, and splits the input light source beam into the object scanning light beam and the reference light beam, and outputs the object scanning light beam and the reference light beam to inspection unit 140 and reference light unit 130, respectively.

For example, optical splitter/coupler 120 of the present embodiment has a prescribed split ratio (for example, a split ratio of about 50:50 to 80:20), and splits the input light source beam based on the split ratio, and outputs the object scanning light beam and the reference light beam to inspection unit 140 and reference light unit 130, respectively.

Further, optical splitter/coupler 120 receives the reflected object light beam reflected on the object in inspection unit 140 and the reflected reference light beam reflected from reference light unit 130.

Then, optical splitter/coupler 120 performs interference the input reflected object light beam and the input reflected reference light beam, and outputs interfering light beam generated by performing the interference to image detection unit 150.

For example, optical splitter/coupler 120 of the present embodiment couples the input reflected object light beam with the input reflected reference light beam to perform interference of the input reflected object light beam and the input reflected reference light beam based on a prescribed coupling ratio (for example, a coupling ratio of about 50:50 to 80:20), and outputs the interfering light beam to image detection unit 150.

Basically, reference light unit 130 is a unit for generating the reflected reference light beam as a reference in an optical path having the same length as that of an optical path of the object scanning light (reflected light) beam. Practically, the optical path of the reference light unit has some optical path difference (below-mentioned optical path difference τ) from the optical path of the object scanning light (reflected light) beam based on the depth required for a diagnosis by the light source beam.

Specifically, reference light unit 130 of the present embodiment has: a first polarization control portion 131 which controls the polarization of the reference light beam which is one of the split light source beams, and the reflected reference light beam which is the other split light source beam and is reflected on retina R, a first transformation lens 132 which transforms the reference light beam outputted from first polarization control portion 131 into parallel light, and which transforms the reflected reference light beam of the parallel light from reflecting mirror RM into focus light; and achromatic lens 133 which performs chromatic aberration.

Further, reference light unit 130 has: water vial 134 which that adjusts chromatic dispersion; reflecting mirror RM which reflects the reference light beam; and a second transformation lens 135 which transforms the reference light beam of the parallel light into focus light and which transforms the reflected reference light beam from the reflecting mirror RM into the parallel light.

In particular, achromatic lens 133 and water vial 134 are used for simulatively setting the same environment as that in which the object scanning light beam (specifically, a reflected object light beam) in inspection unit 140 is irradiated in an eyeball.

Usually, color difference correction lens 133 and water vial 134 are for correcting chromatic aberration or chromatic dispersion generated when eyeball EY is irradiated with a light beam. In reference light unit 130, color difference correction lens 133 and water vial 134 are for generating a light beam on which chromatic aberration or chromatic dispersion in inspection unit 140 is simulatively performed.

Further, first polarization control portion 131 is used for polarizing the reflected reference light beam and the reference light beam individually in order not to perform interference the reflected reference light beam and the reference light beam.

Inspection unit 140 measures the wavefront aberration of the reflected object light beam reflected on a cornea inherently having distortion of an eyeball EY, in an eyeball EY being moved when inspection, or the like. Further, inspection unit 140 adjusts the mirror surface of deformable mirror 145 based on aberration detected by the measurement in order to perform feedback control based on the detected results.

Specifically, inspection unit 140 of the present embodiment has: a second polarization control portion 141 which controls the polarization of the object scanning light beam which is one of the split light source beams and the reflected object light beam which is the other split light source beam and is reflected on retina R; and transformation lens 142 which transforms the object scanning light beam outputted from second polarization control portion 141 into parallel light, and transforms the reflected object light beam of parallel light from retina R into focus light.

Further, inspection unit 140 has: wavefront sensor 143 detecting the wavefront aberration of the reflected object light beam; prism 144 for sensor which splits the reflected object light beam and outputs a part of the split reflected object light beam to wavefront sensor 143; deformable mirror 145; two-axis galvanometer 146; and a pair of concave mirror 147. For example, wavefront sensor 143 of the present embodiment serves as a wavefront sensor of the present invention; and deformable mirror 145 serves as an image location adjusting unit and a deformable mirror of the present invention. For example, concave mirror 147 of the present embodiment serves as an image location adjusting unit and a concave mirror of the present invention; and two-axis galvanometer 146 serves as a beam angle adjusting unit of the present invention.

Similar to first polarization control portion 131, second polarization control portion 141 is used for polarizing the reflected object light beam and the object scanning light beam individually in order not to perform interference the reflected object light beam and the object scanning light beam.

Wavefront sensor 143 of the present embodiment is configured by a Shack-Hartmann sensor, and detects the wavefront aberration based on a light beam on the returning path of the reflected object light beam reflected on retina R.

Deformable mirror 145 is configured so that the shape of mirror surface is controlled by wavefront sensor 143, and reflects the object scanning light beam, which becomes a parallel light by transformation lens 142 for the inspection unit, and the reflected object light beam reflected on retina R in individual directions.

Further, deformable mirror 145 performs a prescribed mirror movement (a mirror surface movement which provides the object scanning light beam with a small vibration) for disturbing the object scanning light beam under a prescribed control.

In the present embodiment, even when the object scanning light beam is disturbed, a small vibration of the object scanning light beam (that is, a small vibration of a reflected object light beam) in an inspection process such as a CCD of scanning camera 154 can be corrected in the calculation of the interference intensity as mentioned below. On the other hand, by providing an object scanning light beam (reflected object light beam) with this small vibration, the contrast of speckle noise can be reduced.

Under the control of a controlling portion which is not illustrated, two-axis galvanometer 146 is configured so that the object scanning light beam is reflected on retina R, the object scanning light beam is swept (moved) in a first direction (transverse direction) which is nearly parallel to the retina forming surface on which retina R is formed, and the object scanning light beam is swept (moved) in a second direction (longitudinal direction) nearly parallel to the retina forming surface and nearly perpendicular to the first direction.

For example, as shown in FIGS. 3(A) and (B), two-axis galvanometer 146 of the present embodiment has: a single scanning mirror 146a which can move in a transverse direction and a longitudinal direction of the retina forming surface, centering around a non-optical axis of the object scanning light beam, in order to sweep the object scanning light beam on retina R; first galvanometer 146b which controls the movement of the scanning mirror 146a in a first direction corresponding the transverse direction of the retina forming surface; and second galvanometer 146c which controls the movement of scanning mirror 146a in a second direction corresponding the longitudinal direction of the retina forming surface. For example, scanning mirror 146a of the present embodiment serves as a scanning mirror of the present invention, and the first galvanometer 146b and the second galvanometer 146c serves as a galvanometer of the present invention.

In particular, second galvanometer 146c holds first galvanometer 146b by blanket 146d, and is configured so that, when scanning mirror 146a revolves, whole first galvanometer 146b revolves.

A pair of concave mirrors 147 are configured so that the object scanning light beam swept by two-axis galvanometer 146 is input and focused in eyeball EY to form an image on retina R.

The reflected object light beam reflected on retina R enters optical distributor/coupler 120 through the above-mentioned opposite path (that is, returning path).

Image detection unit 150 extracts wavelengths from the interfering light beam for each scanning point (each point on retina R scanned in the transverse direction and the longitudinal direction of the retina forming surface) to calculate the interference intensity in each of the extracted wavelengths. Further, image detection unit 150 calculates light intensity data in the depth direction (data representing reflectance distribution in the depth direction) in order to be displayed based on the calculated interference intensity in each of the extracted wavelengths.

Usually, the optical path difference with the reflected reference light beam varies depending on the point of the retina on which the object scanning light beam is reflected. As a result, the interference intensity varies for each of the extracted wavelengths.

Therefore, image detection unit 150 of the present embodiment detects the varied interference intensities, and performs Fourier transformation based on the interference intensities which are data on wavelength domain of each of the extracted wavelengths, in order to transform the data on the wavelength domain into data on space domain. Namely, image detection unit 150 is configured that light intensity data in the depth direction of a retina can be calculated.

Specifically, image detection unit 150 of the present embodiment receives the interfering light beam which is generated by coupling the reflected object light beam transmitted from inspection unit 140 and the reflected reference light beam transmitted from reference light unit 130 to perform the interference.

Further, image detection unit 150 includes: a third polarization control portion 151 which controls the polarization of the interfering light beam; transformation lens 152 for image detection unit which transforms the polarized interfering light beam into parallel light; and grating section 153 which disperses the interfering light beam which is the parallel light for each of wavelengths.

Also, image detection unit 150 includes: scanning camera 154 which detects the interference intensity in each of the wavelengths of the interfering light beam; image generator 155 which calculates light intensity data based on the detected interference intensity of each of wavelengths in order to generate a three-dimensional image of retina R; and display 156 which displays the three-dimensional image data of retina R. For example, scanning camera 154 of the present embodiment serves as a detecting unit of the present invention, and image generator 155 serves as a calculating unit and a forming unit of the present invention.

Next, by FIGS. 4 (A) to (C), a calculation method which calculates a light intensity data of retina R in the depth direction based on the interference intensity data for each of the wavelength of the interfering light beam will be described.

FIGS. 4 (A) to (C) are drawings illustrating the calculation method of interference intensities of a reflected reference light beam and a reflected object light beam.

Light object scanning light beam Ep(t) can be represented by Formula 1. In Formula 1, s(Z) represents the reflection scattering characteristics caused by structure of retina R when the depth direction of an object, or the optical axis direction, is used as z axis, and (E(t)) represents a light beam emitted from light source unit 110.

$$Ep(t) = E(t) \otimes s(t) \qquad \text{[Formula 1]}$$

The symbol of "x" in "○" represents convolution. Formula 1 is represented by a function of time, because the direction of the z axis and the propagation direction are the same, and s(z) is represented by a function s(t) due to the conversion of the propagation direction into time.

There is optical path difference (t) in advance between reference light unit 130 and inspection unit 140, and a light amplitude signal of the reflected reference light beam and the reflected object light beam which is input to optical splitter/coupler 120 is shown in FIG. 4(A).

The light interference intensity of the reflected reference light beam and the reflected object light beam which are dispersed by grating section 153 and which are used to perform Fourier transform, or the spectral interference fringe (E(w)=F[Ep(t)]), is detected by scanning camera 154 (see FIG. 4(B)).

Further, the relation between Fourier interfering signal F[I] which is the Fourier transform of an interfering signal [I] and the spectral interference fringe is shown in Formula 2, where E* represents the complex conjugate.

$$F[I(\omega)] = |F[Ep(\omega)] + F[Ep(\omega)]|^2 \quad \text{[Formula 2]}$$
$$= |F[Ep(\omega)]|^2 + |F[Ep(\omega)]|^2 +$$
$$F[Ep(\omega)]F[Er^*(\omega)] +$$
$$F[Ep^*(\omega)]F[Er(\omega)]$$

Furthermore, Formula 2 can be represented by Formula 3 based on a correlation operation (*).

$$F[I(\omega)] = Ep(t)*Ep^*(t) + Ep(t)*Er^*(t) + Ep(t)*Ep^*(t) + Ep(t)*Er^*(t) \quad \text{[Formula 3]}$$

The first term and the second term in the right side of formula 3 represent the self-correlation signal of the reflected reference light beam and the reflected object light beam, respectively, and the self-correlation signal has the peak in the center in FIG. 4(C). Further, the third term and the fourth term in the right side of Formula 3 represent the cross-correlation signal of the reflected reference light beam and the reflected object light beam, respectively, and the cross-correlation signal has the components emerged in left-right symmetry at positions spaced apart from the self-correlation signal in FIG. 4(C).

The third term [$I_{3rd}$] in the right side of formula 3 is represented by Formula 4 based on the relation of Formula 1. Since the reference light beam reflects on a plane mirror to become the reflected reference light beam and thus {Er(t)=E(t)}, the third term represented by a convolution of the self-correlation function of the light source (light source beam) and the structure in the optical axis direction (so-called depth direction).

$$I_{3rd} = (Er(t)*E(t)) \otimes s(t) \quad \text{[Formula 4]}$$

Specifically, E(t) is regarded as a delta function when the pulse width of the light source beam is sufficiently small or the spectrum distribution is sufficiently wide. Therefore, the data in the depth direction can be obtained by the data of the interference intensity without scanning the retina in the depth direction in the spectrum domain, because the intensity of the cross-correlation signal represents the reflection scattering characteristics of the object in the depth direction.

The resolution ($\Delta z$) in the depth direction can be represented as Formula 5 using center wavelength $\lambda$ of the light source beam and wavelength width $\Delta\lambda$, where "$\sigma$" represents the broadening width of a Gaussian-distributed wavelength.

$$\Delta z = 2\sqrt{2\ln 2}\sigma = \frac{2\ln 2}{\pi} \frac{\lambda^2}{\Delta\lambda} \quad \text{[Formula 5]}$$

As described above, optical coherence eye-fundus tomography device 100 of the present embodiment can use a reflected object light beam which only includes a simple aberration such as astigmatism, without a complex aberration generated in the cornea crystalline lens of eyeball EY or the like. In other words, optical coherence eye-fundus tomography device 100 can use the reflected object light beam having a wavefront aberration represented by third order or lower terms in Zernike polynomials. Therefore, the aberration included the reflected object light beam can be easily corrected.

Therefore, optical coherence eye-fundus tomography device 100 of the present embodiment can calculate the accurate interference intensity in each of wavelengths of the interfering light beam, and generate an accurate three-dimensional image of retina R based on the calculated reflected intensity data. As a result, optical coherence eye-fundus tomography device 100 can have a high resolution for the image of retina R and a good operability, and be built using fewer components, as well as be miniaturized and be produced at a low cost.

Further, it is difficult for any optical components to have a 100% transparency or 100% reflectance and the light quantity decreases for every optical component through which a light goes. Therefore, optical coherence eye-fundus tomography device 100 can improve loss of light quantity when being built using fewer components.

In particular, optical coherence eye-fundus tomography device 100 of the present embodiment can scan the object scanning light beam on retina R, using a single mirror in two-axis galvanometer 146. Therefore, optical coherence eye-fundus tomography device 100 can be built using fewer components, as well as be miniaturized and be produced at a low cost.

Further, optical coherence eye-fundus tomography device 100 of the present embodiment can use the reflected object light beam having a wavefront aberration represented by third order or lower terms in Zernike polynomials. Therefore, optical coherence eye-fundus tomography device 100 can use the reflected object light beam having the wavefront aberration which can be corrected by only a low order aberration and by only deformable mirror 145 without a high order aberration in Zernike polynomials Additionally, optical coherence eye-fundus tomography device 100 of the present embodiment can reduce the contrast of speckle noise by disturbing the wavefront of the reflected object light beam by moving deformable mirror 145.

Second Embodiment

Next, by FIG. 5, the second embodiment of optical coherence eye-fundus tomography device 100 according to the present invention will be described.

FIG. 5 is a block diagram illustrating the configuration of optical coherence eye-fundus tomography device 100 in the present embodiment.

The optical coherence eye-fundus tomography device 100 of the present embodiment is the same as in the first embodiment except for a pair of concave mirrors. Optical coherence eye-fundus tomography device 100 of the present embodiment has at least one of unique feature that a pair of transformation lenses, in place of a pair of concave mirrors of the first embodiment, which is used to input in eyeball EY, the object light beam swept by a two-axis galvanometer in a detection unit, and to focus the object light beam on retina R, in order to form an image on retina R in eyeball EY.

The same members as in the first embodiment has the same number as in the first embodiment, and the description thereof will be left out.

As shown in FIG. 5, inspection unit 240 of the present embodiment has: a second polarization control portion 141 which controls the polarization of the object scanning light beam which is one of the split light source beams and a reflected object light beam which is the other split light source beam and is reflected on retina R; transformation lens 142 for inspection unit; wavefront sensor 143; prism 144 for sensor; deformable mirror 145; two-axis galvanometer 146; and a pair of transformation lenses 241 for adjusting the formation of the image. For example, transformation lenses 241 for adjusting the formation of the image serve as a pair of convex lenses which forms an image on a retina by focusing an object light beam of the present invention.

The pair of transformation lenses 241 for imaging are a pair of convex lenses, and are used to input in eyeball EY, the object light beam swept by two-axis galvanometer 146, and to focus the object light beam on retina R, in order to form an image on retina R in eyeball EY.

As described above, in the same manner as in the first embodiment, optical coherence eye-fundus tomography device 100 of the present embodiment can use a reflected object light beam which only includes a simple aberration such as astigmatism, without a complex aberration generated in the cornea or crystalline lens of eyeball EY or the like. In other words, optical coherence eye-fundus tomography device 100 can use the reflected object light beam having a wavefront aberration represented by third order or lower terms in Zernike polynomials. Therefore, the aberration included the reflected object light beam can be easily corrected.

Therefore, optical coherence eye-fundus tomography device 100 of the present embodiment can calculate the accurate interference intensity in each of wavelengths of the interfering light beam, and generate an accurate three-dimensional image of retina R based on the calculated reflected intensity data. As a result, optical coherence eye-fundus tomography device 100 can have a high resolution for the image of retina R and a good operability, and be built using fewer components, as well as be miniaturized and be produced at a low cost.

Further, it is difficult for any optical components to have a 100% transparency or 100% reflectance and the light quantity decreases for every optical component through which a light goes. Therefore, optical coherence eye-fundus tomography device 100 can improve loss of light quantity when being built using fewer components.

In particular, optical coherence eye-fundus tomography device 100 of the present embodiment can sweep the object scanning light beam on retina R, using a single mirror in two-axis galvanometer 146. Therefore, optical coherence eye-fundus tomography device 100 can be built using fewer components, as well as be miniaturized and be produced at a low cost.

Further, optical coherence eye-fundus tomography device 100 of the present embodiment can use the reflected object light beam having a wavefront aberration represented by third order or lower terms in Zernike polynomials. Therefore, optical coherence eye-fundus tomography device 100 can use the reflected object light beam having the wavefront aberration which can be corrected by only a low order aberration and by only deformable mirror without a high order aberration in Zernike polynomials.

Additionally, optical coherence eye-fundus tomography device 100 of the present embodiment can reduce the contrast of speckle noise by disturbing the wavefront of the reflected object light beam by moving deformable mirror 145.

Third Embodiment

Next, by FIG. 6, the third embodiment of optical coherence eye-fundus tomography device 100 according to the preset invention will be described.

FIG. 6 is a block diagram illustrating the configuration of optical coherence eye-fundus tomography device 100 in the present embodiment.

Optical coherence eye-fundus tomography device 100 of the present embodiment is the same as in the first embodiment except for a pair of transformation lenses. Optical coherence eye-fundus tomography device of the present embodiment has at least one of unique feature that a pair of transformation lenses is used to vary the distance between these lenses in place of the deformable mirror and the pair of concave mirrors.

The same members as in the first embodiment has the same number as in the first embodiment, and the description thereof will be left out.

As shown in FIG. 5, inspection unit 340 of the present embodiment has: second polarization control portion 141 which controls the polarization of the object scanning light beam which is one of the split light source beams and a reflected object light beam which is the other split light source beam and is reflected on retina R; transformation lens 142 for inspection unit; wavefront sensor 143; prism 144 for sensor; two-axis galvanometer 146; a pair of moving lenses 341; and lens 342 for adjusting the formation of the image. For example, the pair of moving lenses 341 of the present embodiment serves as a pair of convex lenses of the present invention, and lens 342 for adjusting the formation of the image serves as a lens by which an object light beam of the present invention forms an image on retina R.

The pair of moving lenses 341 is cylindrical lenses. For example, one of the cylindrical lenses which is disposed on the side of eyeball EY moves in the depth direction based on the control of wavefront sensor 143, and revolves centering around the optical axis of the object scanning light beam.

Moving lenses 341 are used to perform aberration correction of astigmatism. For example, moving lenses 341 is used to adjust the distance between the moving lenses 341 in a direction of the axis of the ellipsoid which is the wavefront of astigmatism.

For example, lens 342 for adjusting the formation of the image has a concave lens and a plano-convex lens which is plane on one side (the side of eyeball EY). Further, lens 342 for adjusting the formation of the image is used to input the object light beam scanned by two-axis galvanometer 146 in eyeball EY, and to focus the object light beam on retina R, in order to form an image on retina R in eyeball EY.

As described above, in the same manner as in the first embodiment, by optical coherence eye-fundus tomography device 100 of the present embodiment can use a reflected object light beam which only includes a simple aberration such as astigmatism, without a complex aberration generated in the cornea or crystalline lens of eyeball EY or the like. In other words, optical coherence eye-fundus tomography device 100 can use the reflected object light beam having a wavefront aberration represented by third order or lower terms in Zernike polynomials. Therefore, the aberration included the reflected object light beam can be easily corrected.

Therefore, optical coherence eye-fundus tomography device 100 of the present embodiment can calculate the accurate interference intensity in each of wavelengths of the interfering light beam, and generate an accurate three-dimensional image of retina R based on the calculated reflected intensity data. As a result, optical coherence eye-fundus tomography device 100 can have a high resolution for the image of retina R and a good operability, and be built using fewer components, as well as be miniaturized and be produced at a low cost.

Further, it is difficult for any optical components to have a 100% transparency or 100% reflectance and the light quantity decreases for every optical component through which a light goes. Therefore, optical coherence eye-fundus tomography device 100 can improve loss of light quantity when being built using fewer components.

In particular, optical coherence eye-fundus tomography device 100 of the present embodiment can scan the object scanning light beam on retina R, using a single mirror in two-axis galvanometer 146. Therefore, optical coherence eye-fundus tomography device 100 can be built using fewer components, as well as be miniaturized and be produced at a low cost.

Further, optical coherence eye-fundus tomography device 100 of the present embodiment can use the reflected object light beam having a wavefront aberration represented by third order or lower terms in Zernike polynomials. Therefore, optical coherence eye-fundus tomography device 100 can use the reflected object light beam having the wavefront aberration which can be corrected by only a low order aberration and by only deformable mirror 145 without a high order aberration in Zernike polynomials.

DESCRIPTION OF THE REFERENCE NUMERALS 100 optical coherence eye-fundus tomography device
110 light source unit
111 irradiation source
112 calibration section
BT optical isolator
120 optical splitter/coupler (optical splitter)
130 reference light unit (reference light beam unit)
131 first polarization control section
132 first transformation lens
133 achromatic lens
134 water vial
135 second transformation lens
RM reflecting mirror
140,240,340 inspection unit (adaptive optics measurement unit)
141 second polarization control section
142 transformation lens for inspection unit
143 wavefront sensor
144 prism for sensor
145 deformable mirror (image location adjusting unit)
146 two-axis galvanometer
146a scanning mirror
146b first galvanometer
146c second galvanometer
146d blanket
147 (147a,147b) concave mirror (image location adjusting unit)
EY eyeball
R retina
150 image detection unit
151 third polarization control section
152 transformation lens for image detection unit
153 grating section
154 scanning camera (detecting unit)
155 image generator (calculating unit, generation unit)
156 display
241 transformation lenses for adjusting the formation of the image (image location adjusting unit)
341 a pair of moving lenses (image location adjusting unit)
342 lens for adjusting the formation of the image (image location adjusting unit)

The invention claimed is:

1. A three-dimensional retina image generator comprising:
a light source unit having a light source;
a light splitter that splits an outgoing light beam emitted from the light source into a reference light beam and an object light beam;
a reference light beam unit that has a reference mirror and reflects the reference light beam, which is inputted therein, by the reference mirror;
an adaptive optics measurement unit that irradiate a retina of an eyeball with the object light beam inputted therein, and that outputs a light scattered on the retina as a reflected object light beam with compensating aberration generated due to the structure of the eyeball, the retina of the eyeball being an object to be measured;
a detecting unit that performs interference of the reflected reference light beam and the reflected object light beam, and that detects interference intensity in each of wavelengths of interfering light beam generated by performing the interference;
a calculating unit that calculates reflected intensity data of the retina in a depth direction nearly parallel to an incident direction by performing a Fourier transform on the detected interference intensity in each of the wavelengths of interfering light beam, the incident direction being a direction in which the object light beam enters the retina; and
a generation unit that generates the three-dimensional image of the retina based on the calculated reflected intensity data,
wherein the adaptive optics measurement unit has:
a wavefront sensor that detects a wavefront of the reflected object light beam;
an image location adjusting unit that has a deformable mirror and that adjusts an image location of the object light beam based on the wavefront of the reflected object light beam, the deformable mirror being a mirror as a single mechanical element in order to only compensate low-order wave aberration including focus correction based on the wavefront of the reflected object light beam detected by a wavefront sensor, and
a beam angle adjusting unit that adjusts an angle of the object light beam with respect to the image location on the retina in order to scan the retina by the object light beam, and
wherein the light source unit emits the outgoing light beam that has a depth of focus of not less than 300 μm and not more than 400 μm, and resolution that is between 3 μM×3 μm and 6 μm×6 μm or higher in a planar direction perpendicular to a traveling direction of the outgoing light beam.

2. The three-dimensional retina image generator according to claim 1, wherein the beam angle adjusting unit comprises:
a single scanning mirror that is capable of moving in two directions in order to sweep the object light beam in a first direction and in a second direction, the first direction being nearly parallel to a retina forming surface on which the retina is formed, the second direction being nearly parallel to the retina forming surface and nearly perpendicular to the first direction; and
a galvanometer that controls movement of the scanning mirror in the first direction and the second direction.

3. The three-dimensional retina image generator according to claim 1, wherein the image location adjusting unit only comprises:

the deformable mirror; and
a concave mirror that forms an image on the retina by focusing the object light beam reflected by the deformable mirror on the retina.

4. The three-dimensional retina image generator according to claim 1, wherein
a mirror surface of deformable mirror is deformed based on the wavefront of the reflected object light beam detected by a wavefront sensor, and
the image location adjusting unit has a convex lens that forms an image on the retina by focusing the object light beam reflected by the deformable mirror on the retina.

5. The three-dimensional retina image generator according to claim 2, wherein the image location adjusting unit only comprises:
the deformable mirror; and
a concave mirror that forms an image on the retina by focusing the object light beam reflected by the deformable mirror on the retina.

6. The three-dimensional retina image generator according to claim 2, wherein
a mirror surface of deformable mirror is deformed based on the wavefront of the reflected object light beam detected by a wavefront sensor, and
the image location adjusting unit has a convex lens that forms an image on the retina by focusing the object light beam reflected by the deformable mirror on the retina.

7. A three-dimensional retina image generator comprising:
a light source unit having a light source;
a light splitter that splits an outgoing light beam emitted from the light source into a reference light beam and an object light beam;
a reference light beam unit that has a reference mirror and reflects the reference light beam, which enters the reference light beam, by the reference mirror;
an adaptive optics measurement unit that irradiate a retina of an eyeball with the object light beam entering the adaptive optics measurement unit, and that outputs a light scattered on the retina as a reflected object light beam with compensating the aberration generated due to the structure of the eyeball, the retina of the eyeball being an object to be measured;
a detecting unit that performs interference of the reflected reference light beam and the reflected object light beam, and that detects interference intensity in each of wavelengths of interfering light beam generated by performing the interference;
a calculating unit that calculates reflected intensity data of the retina in a depth direction nearly parallel to an incident direction in which the object light beam enters the retina by performing a Fourier transform on the detected interference intensity in each of the wavelengths of interfering light beam; and
a generation unit that generates the three-dimensional image of the retina based on the calculated reflected intensity data,
wherein the adaptive optics measurement unit has
a wavefront sensor that detects wavefront of the reflected object light beam;
an image location adjusting unit that adjusts an image location of the object light beam based on the wavefront of the reflected object light beam detected by the wavefront sensor; and
a beam angle adjusting unit that adjusts an angle of the object light beam with respect to the image location on the retina in order to scan the retina by the object light beam, and
wherein the light source unit emits the outgoing light beam that has a depth of focus of not less than 300 µm and not more than 400 µm, and resolution that is between 3 µm×3 µm and 6 µm×6 µm or higher in a planar direction perpendicular to a traveling direction of the outgoing light beam.

8. The three-dimensional retina image generator according to claim 7, wherein the image location adjusting unit comprises:
a pair of convex lenses, distance between the convex lenses varying based on wavefront of the reflected object light beam detected by the wavefront sensor, and
a lens that forms an image on the retina by focusing the object light beam reflected by the deformable mirror on the retina.

* * * * *